(12) United States Patent
Curtis

(10) Patent No.: US 8,333,761 B2
(45) Date of Patent: *Dec. 18, 2012

(54) ELECTROSURGICAL INSTRUMENT AND SYSTEM

(75) Inventor: Richard James Curtis, Newport (GB)

(73) Assignee: Gyrus Medical AG, Cardiff (GB)

( * ) Notice: Subject to any disclaimer, the term of this patent is extended or adjusted under 35 U.S.C. 154(b) by 605 days.

This patent is subject to a terminal disclaimer.

(21) Appl. No.: 12/585,457

(22) Filed: Sep. 15, 2009

(65) Prior Publication Data

US 2010/0082026 A1 Apr. 1, 2010

Related U.S. Application Data

(60) Provisional application No. 61/136,850, filed on Oct. 8, 2008.

(30) Foreign Application Priority Data

Sep. 30, 2008 (GB) .................................. 0817920.2

(51) Int. Cl.
*A61B 18/14* (2006.01)
(52) U.S. Cl. ............................................ 606/37; 606/41
(58) Field of Classification Search .................... 606/34, 606/41, 37
See application file for complete search history.

(56) References Cited

U.S. PATENT DOCUMENTS

| | | | |
|---|---|---|---|
| 3,970,088 A * | 7/1976 | Morrison ......................... | 606/48 |
| 5,269,780 A | 12/1993 | Roos | |
| 6,004,319 A | 12/1999 | Goble et al. | |
| 6,203,542 B1 * | 3/2001 | Ellsberry et al. ................ | 606/41 |
| 6,228,082 B1 | 5/2001 | Baker et al. | |
| 6,558,379 B1 * | 5/2003 | Batchelor et al. ............... | 606/41 |
| 6,663,626 B2 * | 12/2003 | Truckai et al. .................. | 606/41 |
| 6,984,231 B2 | 1/2006 | Goble et al. | |

(Continued)

FOREIGN PATENT DOCUMENTS

EP 1 050 278 11/2000

(Continued)

OTHER PUBLICATIONS

International Search Report for PCT/GB2009/002194 mailed Dec. 30, 2009.

(Continued)

*Primary Examiner* — Michael Peffley
*Assistant Examiner* — Daniel Fowler
(74) *Attorney, Agent, or Firm* — Nixon & Vanderhye PC

(57) ABSTRACT

An electrosurgical system includes an electrosurgical instrument and an electrosurgical generator, the instrument having a longitudinal axis and including at least first, second and third electrodes. The electrodes are spaced from each other by one or more insulating members therebetween, the spacing between the first and third electrodes being greater than that between the first and second electrodes. The electrosurgical generator includes a source of radio frequency energy capable of producing either a coagulating RF waveform or a cutting RF waveform and has first second and third output connections connected to the first, second and third electrodes respectively of the electrosurgical instrument. The generator further includes a switching means, and a controller, the controller being such that when a cutting RF waveform is selected, the switching means directs the cutting RF waveform between the first and second output connections and hence the first and second electrodes. When a coagulating RF waveform is selected, the switching means directs the coagulating RF waveform between the first and third output connections and hence the first and third electrodes.

17 Claims, 5 Drawing Sheets

U.S. PATENT DOCUMENTS

| | | |
|---|---|---|
| 2002/0095152 A1 | 7/2002 | Ciarrocca et al. |
| 2003/0009164 A1 | 1/2003 | Woloszko et al. |
| 2003/0014051 A1 | 1/2003 | Woloszko |
| 2003/0040744 A1 | 2/2003 | Latterell et al. |
| 2003/0097126 A1 | 5/2003 | Woloszko et al. |
| 2003/0163123 A1 | 8/2003 | Goble et al. |
| 2003/0163124 A1* | 8/2003 | Goble .............................. 606/37 |
| 2005/0043728 A1 | 2/2005 | Ciarrocca |
| 2005/0124987 A1 | 6/2005 | Goble |

FOREIGN PATENT DOCUMENTS

| | | |
|---|---|---|
| EP | 1 112 720 | 7/2001 |
| WO | 99/52459 | 10/1999 |
| WO | WO2004/078051 A2 | 9/2004 |
| WO | 2006/051252 | 5/2006 |
| WO | WO2008/043074 A2 | 4/2008 |

OTHER PUBLICATIONS

Written Opinion for PCT/GB2009/002194 mailed Dec. 30, 2009.
Search Report issued in Priority Application No. GB0817920.2, filed Sep. 30, 2008 [Date of Search: Jan. 29, 2009].
International Search Report for corresponding International Application No. PCT/GB2011/000101 mailed Apr. 19, 2011.
Written Opinion for corresponding International Application No. PCT/GB2011/000101 mailed Apr. 19, 2011.

* cited by examiner

ELECTROSURGICAL INSTRUMENT AND SYSTEM

CROSS-REFERENCE TO RELATED APPLICATIONS

This application claims the benefit of Provisional Application No. 61/136,850, filed Oct. 8, 2008, and U.K. Patent Application No. 0817920.2, filed Sep. 30, 2008, the entire contents of which are hereby incorporated by reference in this application.

FIELD OF THE INVENTION

This invention relates to an electrosurgical system comprising a generator and an electrosurgical instrument including electrosurgical electrodes for receiving radio frequency (RF) power from the generator. Such systems are commonly used for the cutting and/or coagulation of tissue in surgical intervention, most commonly in "keyhole" or minimally invasive surgery, but also in "open" surgery.

BACKGROUND OF THE INVENTION

The criteria for an effective cutting instrument are different from those required for an effective coagulating instrument. U.S. Pat. No. 6,004,319 attempts to deal with this problem with a pair of electrodes which are designed to be capable of operating effectively in either a cutting or coagulation mode.

SUMMARY OF THE INVENTION

The present invention provides an alternative solution to the above problem and, according to one aspect, constitutes an electrosurgical system including an electrosurgical instrument and an electrosurgical generator, the electrosurgical instrument including at least first, second and third electrodes, each spaced from each other by insulating members therebetween, the first electrode having a characteristic such that it is adapted to constitute an active electrode, the second electrode having a characteristic such that it is adapted to constitute a first return electrode, and the third electrode having a characteristic such that it is adapted to constitute a second return electrode, the electrosurgical generator including a source of radio frequency energy capable of producing either a coagulating RF waveform or a cutting RF waveform, and first, second and third output connections connected to the first, second and third electrodes respectively of the electrosurgical instrument, the generator further including a switching means and a controller, the controller being such that when a cutting RF waveform is selected, the switching means directs the cutting RF waveform between the first and second output connections and hence the first and second electrodes, and when a coagulating RF waveform is selected, the switching means directs the coagulating RF waveform between the first and third output connections and hence the first and third electrodes.

The generator uses the same electrode as an active electrode for both cutting and coagulation, but switches between using the first return electrode when RF cutting is required, and the second return electrode when RF coagulation is required. The first and second return electrodes can be designed so as to be particularly suitable for their intended purpose, and there is accordingly no need to use the same return electrode for both cutting and coagulation.

This arrangement differs from the arrangements described in U.S. Pat. No. 6,984,231, as in the present arrangement the same active electrode is used for both cutting and coagulation. In the embodiments of the system disclosed in U.S. Pat. No. 6,984,231, the electrode employed as an active electrode in the cutting operation is not employed at all in the coagulation operation.

Preferably, the spacing between the first and third electrodes is greater than that between the first and second electrodes. Furthermore, the characteristic that adapts the first electrode to constitute an active electrode is preferably the electrode area, as is the characteristic that adapts the second and third electrodes to constitute return electrodes. Preferably, the area of the first electrode is less than that of the third electrode. Conveniently, the area of the first electrode is also less than that of the second electrode. In one arrangement, the area of both the first and second electrodes is less than that of the third electrode.

With the area of the electrodes determining which electrode will constitute the active electrode and which the return electrodes, the instrument is designed such that the distance between the active electrode and the return electrode that is used during the cutting operation is relatively small, so as to promote relatively high electric field intensities over a relatively small area. This promotes effective "firing-up" of the cutting electrode, especially where the instrument is used in a wet field or "underwater electrosurgery" environment, in which the instrument is used immersed in an electrically conductive fluid. Conversely, the instrument is designed such that the distance between the active electrode and the return electrode that is used during the coagulation operation is relatively large, so as to provide coagulation over a relatively large area of tissue. The relatively small electrode separations used for effective known cutting instruments mean that any coagulation produced when these known instruments are used in the coagulation mode is restricted to a very small area, and hence they make very poor coagulators. The benefit of the electrosurgical system described herein is that a small electrode separation is used for cutting, but a larger electrode separation is used for coagulation. Thus both effective cutting and coagulation can be provided from the same instrument, by means of the use of different return electrodes for each operation.

In a convenient arrangement, the third electrode is axially set back with respect to the first and second electrodes along the longitudinal axis of the electrosurgical instrument. Typically, the second electrode is also axially set back with respect to the first electrode along the longitudinal axis of the electrosurgical instrument, so as to provide all three electrodes axially spaced along the instrument. In some arrangements, conceivably more than three electrodes are provided, each additional electrode providing subsequently different degrees of electrode separation, for differing cutting or coagulation effects.

In one convenient arrangement, when a coagulating RF waveform is selected, the switching means directs the coagulating RF waveform between the first output connection and both the second and third output connections and hence the first electrode and both the second and third electrodes. In this way both return electrodes are used in the coagulation process, giving both relatively precise coagulation between the first and second electrodes, and relatively broad coagulation between the first and third electrodes.

Conceivably, the generator is provided with a blend mode in which the switching means directs the cutting RF waveform between the first and second output connections and hence the first and second electrodes, and also directs the coagulating RF waveform between the first and third output connections and hence the first and third electrodes. This provides a combined cutting and coagulation effect, in which tissue is cut and coagulated at the same time. In one arrangement, the generator directs the cutting RF waveform between the first and second output connections and hence the first and second electrodes simultaneously with directing the coagulating RF waveform between the first and third output connections and hence the first and third electrodes. This may require the use of more than one radio frequency source, or the use of RF signals at different frequencies, to avoid the RF cutting waveform interfering with the RF coagulation waveform. Alternatively, the generator alternates rapidly between directing the cutting RF waveform between the first and second output connections and directing the coagulating RF waveform between the first and third output connections. With a sufficiently rapid alternation between the cutting and coagulating waveforms, a simultaneous tissue effect is achieved without the cutting waveform and the coagulating waveform interfering one with the other.

According to an alternative aspect of the invention, there is provided an electrosurgical system including an electrosurgical instrument and an electrosurgical generator, the electrosurgical instrument including at least first, second and third electrodes, each spaced from each other by insulating members therebetween, the electrosurgical generator including a source of radio frequency energy capable of producing either a coagulating RF waveform or a cutting RF waveform, and first second and third output connections connected to the first, second and third electrodes respectively of the electrosurgical instrument, the generator further including a switching means, and a controller, the controller being such that when a cutting RF waveform is selected, the switching means directs the cutting RF waveform between the first and second output connections and hence the first and second electrodes, and when a coagulating RF waveform is selected, the switching means directs the coagulating RF waveform between the first and third output connections and hence the first and third electrodes, the first electrode having a characteristic such that it is adapted to constitute an active electrode, the third electrode having a characteristic such that it is adapted to constitute a return electrode, and the second electrode having a characteristic such that it is adapted to constitute a either an active electrode or a return electrode, depending on the circumstances.

In this way, the second electrode sometimes acts as an active electrode and at other times acts as a return electrode. In one convenient arrangement, the second electrode is adapted to constitute a return electrode when the cutting RF waveform is supplied between the first and second output connections. In the other situation, the second electrode is adapted to constitute an additional active electrode when the coagulating RF waveform is supplied between the first and third output connections. Preferably, the switching means connects the first and second output connections in common when the coagulating RF output is supplied between the first and third output connections. In this arrangement, coagulation can take place between the first and third electrodes, and also between the second and third electrodes.

The invention will be further described, by way of example only, with reference to the accompanying drawings.

DETAILED DESCRIPTION OF THE PREFERRED EMBODIMENTS OF THE INVENTION

Figure 1:
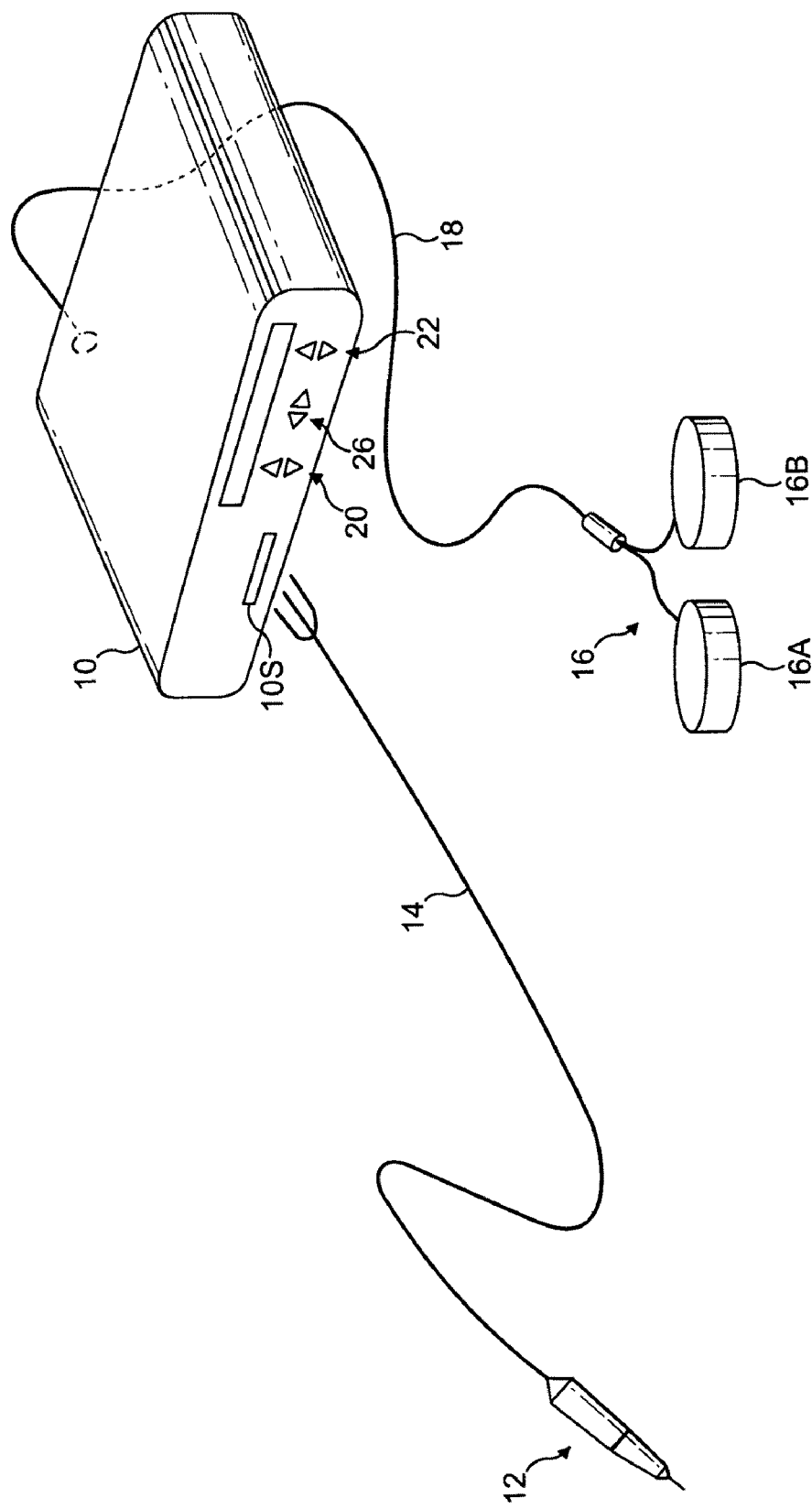
FIG. 1 is a schematic diagram of an electrosurgical system in accordance with the present invention.

Referring to FIG. 1, a generator 10 has an output socket 10S providing a radio frequency (RF) output for an instrument 12 via a connection cord 14. Activation of the generator may be performed from the instrument 12 via a connection in cord 14 or by means of a footswitch unit 16, as shown, connected to the rear of the generator by a footswitch connection cord 18. In the illustrated embodiment footswitch unit 16 has two footswitches 16A and 16B for selecting a coagulation mode and a cutting mode of the generator respectively. The generator front panel has push buttons 20 and 22 for respectively setting coagulation and cutting power levels, which are indicated in a display 24. Push buttons 26 are provided as a means for selection between alternative coagulation and cutting waveforms.

Figure 2:
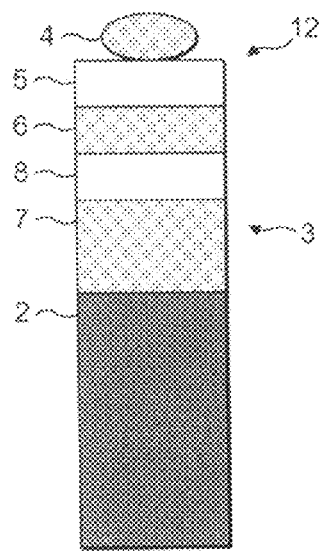
FIG. 2 is a schematic side view of the distal part of an electrosurgical instrument used in the system of FIG. 1.

FIG. 2 shows an embodiment of the instrument 12 in more detail. The instrument 12 has an insulated shaft 2 and a distal region 3. At the very tip of the instrument is an active electrode 4, separated from a first return electrode 6 by an insulating member 5, the insulating member serving to set back the return electrode axially with respect to the active electrode 4. A second return electrode 7 is provided, separated from the first return electrode by an insulating member 8 such that the second return electrode is axially set back with respect to the first return electrode. In this way, the distance between the active electrode 4 and the first return electrode 6 is much smaller than the distance between the active electrode 4 and the second return electrode 7.

The exposed surface area of the active electrode 4 is smaller than that of either the first return electrode 6 or the second return electrode 7. This helps to ensure that the electrode 4 acts as an active electrode and the electrodes 6 and 7 act as return electrodes during the electrosurgical cutting or coagulation process. The electrodes 4, 6 and 7 are connected to the electrosurgical generator 10 via the connection cord 14, where they are connected to different output connections, as will now be described.

Figure 3:
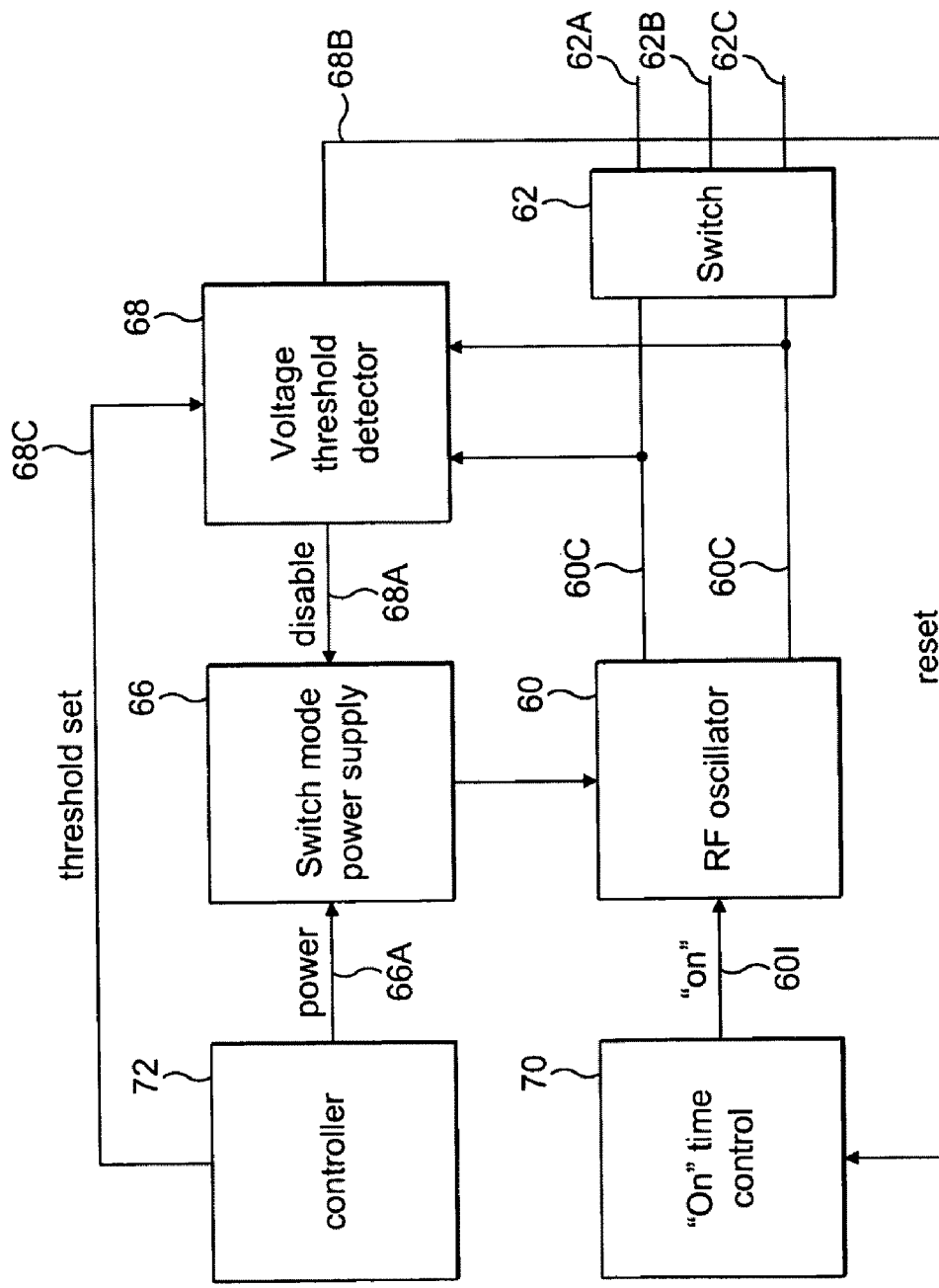
FIG. 3 is a schematic block diagram of an electrosurgical generator used in the system of FIG. 1, FIGS. 4A and 4B are schematic block diagrams of the output stages of the electrosurgical generator of FIG. 3, shown in differing stages of operation.

Referring to FIG. 3, the generator comprises a radio frequency (RF) output stage in the form of a power oscillator 60 having a pair of output lines 60C for coupling via switching circuit 62 to the instrument 12. Switching circuit 62 has first, second and third output connections 62A, 62B and 62C for connection to the electrodes of the instrument, as will be described later. Power is supplied to the oscillator 60 by a switched mode power supply 66.

In the preferred embodiment, the RF oscillator 60 operates at about 400 kHz, with any frequency from 300 kHz upwards into the HF range being feasible. The switched mode power supply typically operates at a frequency in the range of from 25 to 50 kHz. Coupled across the output lines 60C is a voltage threshold detector 68 having a first output 68A coupled to the switched mode power supply 66 and a second output 68B coupled to an "on" time control circuit 70. A micro-processor controller 72 coupled to the operator controls and display (shown in FIG. 1) is connected to a control input 66A of the power supply 66 for adjusting the generator output power by supply voltage variation and to a threshold-set input 68C of the voltage threshold detector 68 for setting peak RF output voltage limits.

In operation, the microprocessor controller 72 causes power to be applied to the switched mode power supply 66 when electrosurgical power is demanded by the surgeon operating an activation switch arrangement which may be provided on a hand-piece or footswitch (see FIG. 1). A constant output voltage threshold is set independently of the supply voltage via input 68C according to control settings on the front panel of the generator (see FIG. 1). Typically, for desiccation or coagulation the threshold is set at a desiccation threshold value between 150 volts and 200 volts. When a cutting or vaporisation output is required the threshold is set to a value in the range of from 250 or 300 volts to 600 volts. These voltage values are peak values. Their being peak values means that for desiccation or coagulation at least it is preferable to have an output RF waveform of low crest factor to give maximum power before the voltage is clamped at the values given. Typically a crest factor of 1.5 or less is achieved.

When the generator is first activated, the status of the control input 601 of the RF oscillator 60 (which is connected to the "on" time control circuit 70) is "on", such that the power switching device which forms the oscillating element of the oscillator 60 is switched on for a maximum conduction period during each RF oscillation cycle. The power delivered to the tissue depends partly on the supply voltage applied to the RF oscillator 60 from the switched mode power supply 66 and partly on the tissue impedance. The voltage threshold for a desiccation output is set to cause trigger signals to be sent to the "on" time control circuit 70 and to the switched mode power supply 66 when the voltage threshold is reached. The "on" time control circuit 70 has the effect of virtually instantaneously reducing the "on" time of the RF oscillator-switching device. Simultaneously, the switched mode power supply is disabled so that the voltage supplied to oscillator 60 begins to fall. The operation of the generator in this way is described in detail in European Published Patent Application No. 0754437, the disclosure of which is hereby incorporated by way of reference.

Figure 4A:
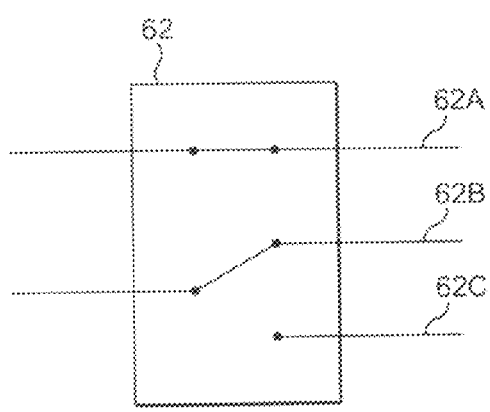

The output connections 62A, 62B and 62C from the generator 10 are electrically connected to the three electrodes 4, 6 and 7 (FIG. 2) respectively, via lead 14. When it is desired to operate the instrument 12 in a cutting mode, footswitch 16A is depressed which causes a signal to be sent to the controller 72 which sets the switching circuit 62 its "cut" position. This is illustrated in FIG. 4A, in which the signals from the oscillator 60 are connected between the first and second output connections 62A, 62B. This means that the RF power signal is applied between the cutting electrode 4 and the first return electrode 6. The third or output connection 62C (and hence second return electrode 7) is not energized.

At the same time as the controller 72 sets the switching circuit to the position in FIG. 4A, it also sends a signal via line 68C to the voltage threshold detector 68 to set the peak output voltage limit to a relatively high "cutting" level. The control of this cutting signal is described in more detail in EP 0754437, referred to earlier. In cutting mode, the output from the generator is a relatively high voltage, with a consequent low current level, and the relatively small distance between the active electrode 4 and 6 and the first return electrode ensures that the electrode assembly fires up and cuts tissue, even if the tip of the instrument is immersed in an electrically-conductive fluid.

Figure 4B:
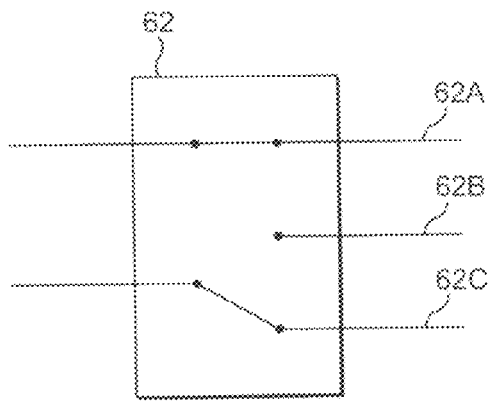

Alternatively, when it is desired to operate the instrument 12 in a coagulation mode, footswitch 16B is depressed which causes the controller 72 to set the switching circuit 62 to its "coag" state, as illustrated in FIG. 4B. In this set-up, the power signals from the oscillator are connected between the first and third output connections 62A, 62C. This means that the RF power signal is applied between the active electrode 4 and the second return electrode 7. At the same time the controller sends a signal to the voltage threshold detector 68 to set the peak output voltage limit to a relatively lower "coagulating" level, again as more particularly described in EP 0754437. In "coag" mode, the output from the generator is a relatively lower voltage, with a corresponding relatively higher current, and the relatively larger distance between the active and second return electrodes 4 and 7 ensures that an effective area of coagulation is produced.

In an alternative switching arrangement (not shown), when the instrument 12 is to be operated in coagulation mode, the switching circuit connects the power signals from the oscillator between the first output connection 62A and both of the second and third output connections 62B and 62C. In this way, both return electrodes 6, 7 are used in the coagulation process, giving both relatively precise coagulation between the active electrode 4 and the first return electrode 6, and relatively broad coagulation between the active electrode 4 and the second return electrode 7.

Figure 5:
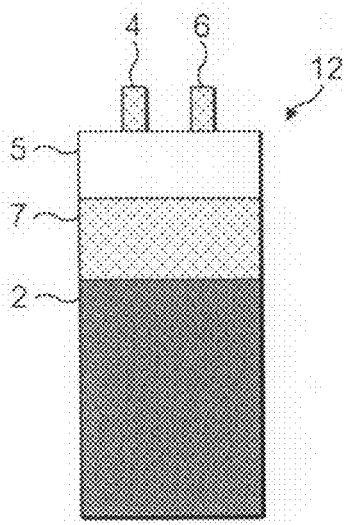
FIG. 5 is a schematic side view of the distal part of an alternative embodiment of electrosurgical instrument used in the system of FIG. 1.

FIG. 5 shows an alternative instrument 12 in which both an active electrode 4 and the first return electrode 6 are located at the distal tip of the instrument. A single insulating member 5 is provided to separate these two electrodes 4, 6 from each other, and also from a second return electrode 7 which is axially set back from the active and first return electrodes 4, 6. The operation of the instrument is similar to that described previously, in that cutting signals from the generator 10 are supplied to the first and second output connections 62A, 62B, and hence to the active and first return electrodes 4, 6. In this way, electrosurgical cutting takes place between the two electrodes 4, 6 at the distal tip of the instrument. In this situation the first return electrode 6 is acting as a return electrode for the cutting operation.

When coagulation is required, the coagulation output from the generator is supplied to the first and third output connections 62A, 62C and hence to the active and second return electrodes 4, 7. Optionally in this arrangement the first and second output connections 62A, 62B can be connected together during the coagulation phase, so that coagulation takes place between either or both of the active and first return electrodes 4, 6 on the one hand, and the second return electrode 7 on the other hand. In this situation, the first return electrode 6 is acting as an additional active electrode for the coagulation operation.

Figure 6:
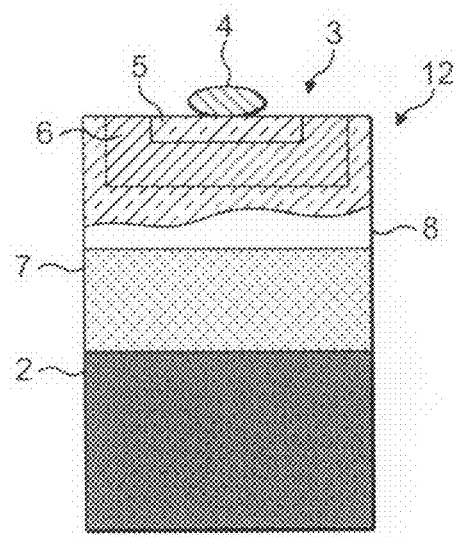
FIG. 6 is a partly sectioned schematic side view of the distal part of a further alternative embodiment of electrosurgical instrument used in the system of FIG. 1.

FIG. 6 shows an alternative embodiment in which the active electrode 4 is present at the distal tip of the instrument 12, and the first return electrode 6 surrounds the active electrode 4 as shown. In this case, the first return electrode 6 has an annular surface exposed on a distally directed surface portion of the instrument distal region 3 The insulating member 5 separates the active electrode 4 from the first return electrode 6, and the other insulating member 8 separates these two electrodes 4, 6 from an axially set-back second return electrode 7. The operation of this device is as previously described, with electrosurgical cutting taking place between the active and first return electrodes 4 and 6 over the relatively short distance therebetween, with electrosurgical coagulation taking place between the active and second return electrodes 4, 7, over a much larger distance.

Figure 7:
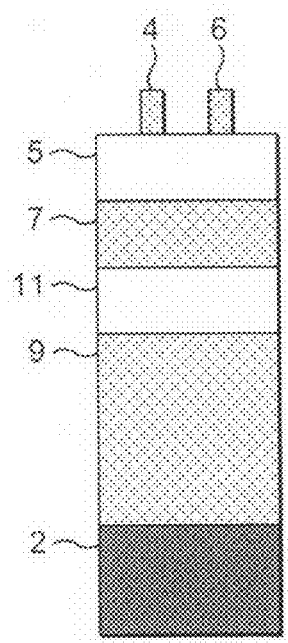
FIG. 7 is a schematic plan view of the distal part of yet another embodiment of electrosurgical instrument used in the system of FIG. 1, and FIGS. 8 and 9 are perspective and sectional side views respectively of a further embodiment of electrosurgical instrument in accordance with the present invention.

FIG. 7 shows a four-electrode instrument, using a combination of the features from previous embodiments shown in FIGS. 2 and 5. An active electrode 4 and first return electrode 6 are both present on the tip of the instrument 12, separated by insulating member 5 from each other and also from a second return electrode 7 which is axially set back from the first two electrodes 4, 6. However, there is additionally provided a third return electrode 9 axially set back from the second return electrode 7 by means of a further insulating member 11. The generator has a further output connection which can be selected by the switching means 62 (see FIG. 3) to connect to the third return electrode 9. In this way, the instrument has three different settings, "cut", "focused coagulation" and "broad coagulation". In the cut mode, the cutting RF waveform is directed between the active electrode 4 and the first return electrode 6. In the focused coagulation mode, a coagulating RF waveform is directed between the active electrode and the second return electrode 7. In the broad coagulation mode, the coagulating RF waveform is directed between the active electrode and the third return electrode 9. In each case, the distance between the active electrode and each respective return electrode increases, such that the broad coagulation takes place over an even larger area of tissue than the focused coagulation.

Figure 8:
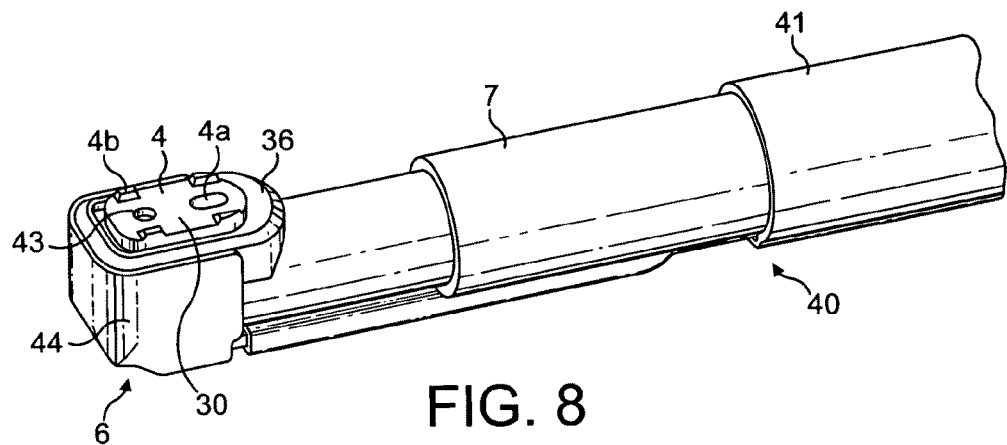
Figure 9:
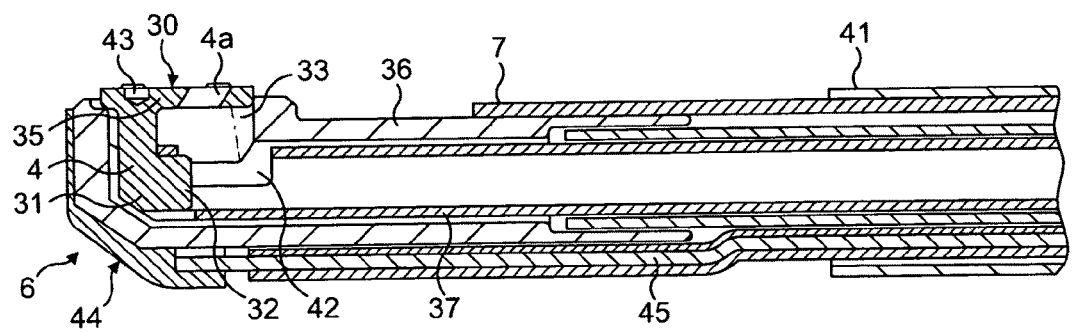

FIGS. 8 and 9 show an alternative embodiment of instrument based on that disclosed in published US Patent Application No. US2009/0048592, the entire contents of which are hereby incorporated by reference. In this instrument, the active electrode 4 is located within a ceramic insulator 36. The active electrode 4 is housed within a chamber 33 provided in the ceramic insulator 36. This tissue treatment electrode 4 is formed of tungsten or an alloy of tungsten and platinum. It is formed with a suction aperture 4a, and is provided with a respective projection 4b at each of its corners, the projections being provided to concentrate the electric field in each of the corners of the active electrode. The projections 4b also serve to create a small separation between the planar surface 30 of the active electrode 4 and the tissue to be treated. This allows conductive fluid to circulate over the planar surface, and avoids overheating of the electrode or the tissue.

As shown in FIG. 9, the active electrode 4 comprises an upper portion 35 including the planar surface 30 and the projections 4b, and a lower portion 31 including a shaped keel portion 32. To assemble the instrument, the active electrode 4 is lowered into a chamber 33 present within the ceramic insulator 36. A suction tube 37 is then pushed forward to locate over the keel portion 32 of the active electrode and secure it in place. The forward movement of the suction tube 37 pushes the active electrode 4 forwardly in the chamber 33, thereby locking the active electrode in place.

In order to reduce the problems of vapour bubble production and to assist with the removal of particulate material (such as tissue debris) from the region surrounding the tissue treatment electrode 4, the instrument is provided with a suction pump (not shown) which can remove vapour bubbles via the shaft of the instrument through the aperture 4a in the active electrode. The suction tube 37 is made of an electrically-conductive material such as stainless steel or gold-plated copper, and connects the suction aperture 4a to the suction pump. The tube 37 also constitutes means for electrically connecting the active electrode 4 to the generator 10.

The return electrode 7 is constituted by the distal end portion of the shaft 40, and a polytetrafluorethylene, a poly-olefin, a polyester or ethylene tetrafluoroethylene sleeve 41 surrounds the proximal portion of the shaft 40 adjacent to the return electrode 7. The suction tube 37 is formed with a longitudinal slot 42 at its distal end. As shown in the figures, the distal end of the suction tube 37 extends into the chamber 33 defined by the ceramic insulator 36 beneath the active electrode 4. The slot 42 is contiguous with the aperture 4a in the active electrode 4, which slopes through the tissue treatment electrode at an angle of approximately 45 degrees. A blind recess 43 is provided in the electrode 4. This recess 43 is provided purely to allow for the automated assembly of the electrosurgical instrument, and does not provide a suction aperture as it does not pass all the way through the electrode 4.

The ceramic insulator 36 is surrounded with a metallic cowl 44, which forms the first return electrode 6 and which is connected via an outer lead 45 to the generator 10, and to the switching circuit 62 described above with reference to FIGS. 4A and 4B. When the instrument is being used to cut tissue, the switching circuit delivers the RF power signal between the active electrode 4 and the cowl 44 (i.e. the first return electrode 6). However, when the instrument is being used to coagulate tissue, the switching circuit delivers the RF power signal between the active electrode 4 and the second return electrode 7. The distance between the active and first electrodes 4, 6 is less than that between the active and second return electrodes 4, 7, so that a relatively small electrode separation exists when the instrument is being used to cut tissue, whereas a relatively larger electrode separation exists when the instrument is being used to coagulate tissue.

It will be appreciated that further combinations of electrodes and generator switching are possible without departing from the scope of the present invention. The instruments can be employed directly contacting tissue as dry-field instruments, or used immersed in a conductive fluid as wet-field instruments. The switching circuit 62 can be used simply to switch between the cut and coagulation modes, or can be used to provide a blended cut and coagulation mode in which it alternates rapidly between the two states, as described in more detail in U.S. Pat. No. 6,966,907, the contents of which are incorporated by reference. Those skilled in the art will appreciate how these different variations can be employed, depending on the requirements of each procedure or surgeon preference.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. An electrosurgical system including:
   an electrosurgical instrument, and
   an electrosurgical generator,
   the electrosurgical instrument including:
      at least first, second and third electrodes, each spaced from each other by insulating members therebetween,
      the first electrode having a characteristic such that it is adapted to constitute an active electrode,
      the second electrode having a characteristic such that it is adapted to constitute a first return electrode, and
      the third electrode having a characteristic such that it is adapted to constitute a second return electrode,
   the electrosurgical generator including:
      a source of radio frequency energy capable of producing either a coagulating RF waveform or a cutting RF waveform, first, second and third output connections connected to the first, second and third electrodes respectively of the electrosurgical instrument, a switch, and a controller, the controller being such that:

when a cutting RF waveform is selected, the switch directs the cutting RF waveform between the first and second output connections, and thereby the first and second electrodes, such that the first electrode is the active electrode and the second electrode is the return electrode, and when a coagulating RF waveform is selected, the switch directs the coagulating RF waveform between the first and third output connections, and thereby, the first and third electrodes, such that the first electrode is the active electrode and the third electrode is the return electrode.

2. The electrosurgical system according to claim 1, wherein the spacing between the first and third electrodes is greater than that between the first and second electrodes.

3. The electrosurgical system according to claim 1, wherein the characteristic that adapts the second and third electrodes to constitute return electrodes is the electrode area.

4. The electrosurgical system according to claim 1, wherein the characteristic that adapts the first electrode to constitute an active electrode is the electrode area.

5. The electrosurgical system according to claim 4, wherein the area of the first electrode is less than that of the third electrode.

6. The electrosurgical system according to claim 5, wherein the area of the first electrode is less than that of the second electrode.

7. The electrosurgical system according to claim 5, wherein the first and second electrodes each have an area that is less than that of the third electrode.

8. The electrosurgical system according to claim 1, wherein the third electrode is axially set back with respect to the first and second electrodes along the longitudinal axis of the electrosurgical instrument.

9. The electrosurgical system according to claim 8, wherein the second electrode is axially set back with respect to the first electrode along the longitudinal axis of the electrosurgical instrument.

10. The electrosurgical system according to claim 1, wherein when a coagulating RF waveform is selected, the switch directs the coagulating RF waveform between the first output connection and both the second and third output connections and hence the first electrode and both the second and third electrodes.

11. The electrosurgical system according to claim 1, wherein the generator is provided with a blend mode in which the switch directs the cutting RF waveform between the first and second output connections and hence the first and second electrodes, and also directs the coagulating RF waveform between the first and third output connections and hence the first and third electrodes.

12. The electrosurgical system according to claim 11, wherein, in the blend mode, the generator alternates rapidly between directing the cutting RF waveform between the first and second output connections and directing the coagulating RF waveform between the first and third output connections.

13. The electrosurgical system according to claim 1, wherein the spacing between the first, active electrode and the third, return electrode is greater than the spacing between the first, active electrode and the second, return electrode, such that, in another mode of operation of the generator, when the coagulating RF waveform is selected, the switch directs the coagulating RF waveform between the first and third output connections, and between the first and second output connections, and thereby, between the first and third electrodes and between the first and second electrodes, such that the spacing between the first and third electrodes allows coagulation over an area of tissue that is broader and less precise than the coagulation allowed by the lesser spacing between the first and second electrodes.

14. The electrosurgical system according to claim 1, wherein the separation between the first, active electrode and the third, return electrode is larger than the separation between the first, active electrode and the second, return electrode, such that, the larger separation between the first and third electrodes is used for coagulation, and the smaller separation between the first and second electrodes is used for cutting.

15. An electrosurgical system including;

an electrosurgical instrument, and an electrosurgical generator, the electrosurgical instrument including at least first, second and third electrodes, each spaced from each other by insulating members therebetween, the first electrode having a characteristic such that during operation of the electrosurgical instrument the first electrode acts as an active electrode, the third electrode having a characteristic such that during operation of the electrosurgical instrument the third electrode acts as a return electrode, and the second electrode having a characteristic such that during operation of the electrosurgical instrument the second electrode can act as either an active electrode or a return electrode, the electrosurgical generator including:

a source of radio frequency energy capable of producing either a coagulating RF waveform or a cutting RF waveform, first, second and third output connections connected to the first, second and third electrodes, respectively, of the electrosurgical instrument, a switch, and a controller, the controller being such that:

in one mode of operation of the generator, when a cutting RF waveform is selected, the switch directs the cutting RF waveform between the first and second output connections, and thereby, the first and second electrodes, such that the first electrode is the active electrode and the second electrode is the return electrode, and in another mode of ration of the generator, when a coagulating RF waveform is selected, the switch directs the coagulating RF waveform between the first and third output connections and between the second and third output connections, and thereby, between the first and third electrodes and between the second and third electrodes, such that the first electrode is the active electrode, the second electrode is an additional active electrode and the third electrode is the return electrode.

16. The electrosurgical system according to claim 15, wherein the switch connects the first and second output connections in common when the coagulating RF output is supplied between the first and third output connections.

17. The electrosurgical system according to claim 15, wherein the characteristic of the second electrode that allows the second electrode to act during operation of the electrosurgical instrument as either an active electrode or a return electrode is that the second electrode is located at a distal tip of the electrosurgical instrument with the first electrode, but separated from the first electrode by one of the insulating members.

* * * * *